United States Patent [19]

Graunke

[11] 4,336,111
[45] Jun. 22, 1982

[54] METHOD FOR DETERMINING THE STRENGTH OF A METAL PROCESSING SOLUTION

[75] Inventor: Donald R. Graunke, Seattle, Wash.

[73] Assignee: The Boeing Company, Seattle, Wash.

[21] Appl. No.: 88,387

[22] Filed: Oct. 25, 1979

Related U.S. Application Data

[63] Continuation-in-part of Ser. No. 957,225, Nov. 2, 1978, abandoned.

[51] Int. Cl.³ ............................................. G01N 27/06
[52] U.S. Cl. .................................... 204/1 T; 156/627; 427/8
[58] Field of Search ............... 204/1 T, 195 R, 195 C, 204/1 C, 129.2; 427/8, 443.1; 156/627, 345

[56] References Cited

U.S. PATENT DOCUMENTS

| | | | |
|---|---|---|---|
| 3,207,678 | 9/1965 | Marsh et al. | 204/195 C X |
| 3,405,041 | 10/1968 | Langermeersch | 204/1 T |
| 3,428,532 | 2/1969 | Banks | 204/1 T |
| 3,922,205 | 11/1975 | McLean et al. | 204/1 T |
| 3,925,168 | 12/1975 | Costas | 204/1 T |
| 4,146,437 | 3/1979 | O'Keefe | 204/1 T |

FOREIGN PATENT DOCUMENTS 1009111 11/1965 United Kingdom ............... 204/1 T

OTHER PUBLICATIONS

T. M. Florence, J. Electroanal. Chem., vol. 27, No. 2, pp. 273–281, (10970).
A. M. Bond et al., Anal. Chem., vol. 43, No. 3, pp. 393–397, (1971).

Primary Examiner—G. L. Kaplan
Attorney, Agent, or Firm—Christensen, O'Connor, Johnson & Kindness

[57] ABSTRACT

Disclosed is a method for determining the strength of a metal processing solution, defined herein to include electroless metal plating solutions and chemical etching solutions wherein a metal is plated onto and stripped from, respectively, the surface of a metal substrate. A pair of electrodes, preferably composed of the metal being plated in the case of an electroless metal plating solution or the metal having been etched in the case of a chemical etching solution, are immersed spaced from one another in the metal processing solution. A voltage is gradually applied across the electrodes and steadily increased. As the voltage is increased, the current flowing between the electrodes in the solution is monitored. The point at which the current first passes through a maximum value and begins to decrease is recorded as a function of time or voltage and is correlated empirically with the strength of the metal processing solution.

13 Claims, 12 Drawing Figures

METHOD FOR DETERMINING THE STRENGTH OF A METAL PROCESSING SOLUTION

CROSS REFERENCE TO RELATED APPLICATION

This application is a continuation-in-part of U.S. application Ser. No. 957,225, filed Nov. 2, 1978 and now abandoned.

BACKGROUND OF THE INVENTION

The present invention relates generally to methods for measuring the strength of a metal processing solution, and more particularly to methods for measuring the plating rate of an electroless metal plating solution and the etching rate of a chemical etching solution.

The method of the present invention is applicable generally to two broad classes of chemical solutions widely used throughout industry. The two classes of chemical solutions include electroless metal plating solutions and chemical etching solutions, as further defined below, and are collectively referred to herein as "metal processing solutions." As also used herein, the "strength" of a metal processing solution refers to the plating rate in the case of an electroless metal plating solution and the etching rate in the case of an etching solution.

More specifically, the term "electroless plating solution" refers to a solution which utilizes a catalytic chemical process to selectively reduce and plate a metal species onto the surface of a catalytic substrate immersed in the solution. Examples of electroless plating solutions widely used in industry include electroless nickel plating solutions and electroless copper plating solutions.

Such electroless plating solutions typically include a reducing agent, such as a hypophosphite salt, and a metallic ionic salt of the metal to be plated. Upon immersion of a substrate having a suitable catalytic surface in the solution, the hypophosphite anions are catalytically oxidized at the substrate surface. The metal cations in the solution are concurrently reduced and plated onto the substrate surface. The reaction is visually observable and is evidenced by the evolution of hydrogen gas from the surface of the substrate. The resulting metal plating is amorphous in character and consists primarily of the reduced metal species together with a relatively small amount of phosphorous. A succinct summary of the chemistry of electroless plating solutions may be found in U.S. Pat. No. 3,375,178 to Locke.

When the metal ions and the reducing agent in an electroless plating solution become depleted beyond a certain point, the strength of the plating solution, as measured by its plating rate, is decreased sufficiently so that it is no longer practical economically to continue using the plating solution. It is then necessary to prepare a fresh solution or add makeup components to raise the strength of the spent solution back to a reasonably acceptable level. The minimum acceptable plating rate, or strength, of an electroless plating solution is commonly referred to as the specification limit of the solution.

Determining whether an electroless plating solution has been depleted beyond its specification limit has been a problem in the past. Several types of tests have been used to determine the strength of electroless plating solutions, but none have proven entirely satisfactory. For example, a straightforward plating rate test may be employed to directly measure the actual plating rate of a given production solution. In such a test, a sample of a standard substrate material having a known surface area is immersed in the plating solution for a predetermined period of time, typically on the order of several hours. The sample is weighed before and after plating. On the basis of the observed weight increase and the surface area of the sample, the plating rate is calculated in units of, for example, milligrams of metal per square centimeter per minute. The primary drawbacks of this method are that it is time consuming and subject to relatively large errors because of the often small difference in the weight of the sample before and after plating.

Alternatively, wet chemical and spectrophotometric analytical techniques have been used to determine the concentration of the active components in electroless plating solutions. Such techniques may, for example, be based on a determination of the concentration of either the metal cations or the hypophosphite ions, each of which vary in concentration continuously as the solution is depleted and which therefore may be empirically correlated with the plating rate of the solution. Such techniques are awkward because they are time consuming and usually require that a sample of solution be removed to a chemical laboratory for analysis. Also, analytical chemical techniques are not entirely satisfactory because the actual strength, or plating rate, of an electroless plating solution is dependent upon a number of factors, including the concentrations of hypophosphite anions, metallic cations, pH and temperature, so that any single one of these factors may not always be relied upon exclusively to give an accurate measure of the plating rate of the solution.

The term "chemical etching solutions" is used herein to refer to a rather wide variety of solutions which act upon a metal substrate to oxidize and dissolve metal from the surface of the substrate. Such solutions range from relatively mild cleaning solutions to relatively strong chemical milling solutions. These solutions contain an oxidizing agent for oxidizing the native metal to a water soluble ionic species. Chemical etching solutions are generally also acidic, although some solutions, for example etching solutions used on aluminum or zinc, may be strongly basic.

One example of a chemical etching solution is a copper stripping solution used to make printed circuit boards. The copper coated circuit boards are masked with a resistant coating having a desired pattern and immersed in a copper stripping solution to etch the metallic copper from the unmasked portions of the board. As another example, a chemical milling solution is typically used in a similar manner on a masked metal substrate to selectively form recessed areas in the surface of the substrate. This technique is particularly useful in forming areas of reduced thickness on large metal panels where it would be impractical to use conventional mechanical milling methods. Finally, other examples of chemical etching solutions include conventional etching or stripping solutions used to roughen or clean the surface of a metal part, or to produce various types of decorative textured surfaces on metal workpieces.

The strength of a chemical etching solution is measured by its etching rate, as expressed, for example, in milligrams of metal etched per square centimeter per minute. The etching rate of such a solution depends upon such factors as the concentration of the oxidizing agent in the solution, the pH of the solution, and the accumulated concentration of metal salts in the solution. In practice, routine use of an etching solution results in gradual depletion of the active components in the solution, with a resulting reduction in its etching rate.

Determination of the actual etching rate of a particular solution is difficult and suffers from many of the same drawbacks as described above with respect to electroless plating solutions. For example, the most straightforward method of measuring the etching rate is to measure the weight loss of a metal sample of known surface area when placed in an etching solution for a predetermined period of time. This method is, however, time consuming and is subject to large errors due to the practical problems associated with precisely measuring a relatively small weight change in a relatively heavy piece of metal. For the reasons discussed above, analytical chemical techniques are also relatively awkward, time consuming and imprecise.

It is therefore an object of the present invention to provide a method for determining the relative or actual strength of a metal processing solution, particularly including the plating rate of an electroless plating solution and the etching rate of a chemical etching solution. More particularly, it is an object of the present invention to provide a method for measuring the strength of a metal processing solution which may be performed in situ and which does not in itself affect the strength of the solution. Further, it is an object of the present invention to provide a method for measuring the strength of a metal processing solution which is fast, simple and which requires no particular expertise or training to practice.

SUMMARY OF THE INVENTION

In accordance with the present invention, a pair of electrodes are immersed in a metal processing solution. A voltage is gradually applied across the electrodes and is steadily increased. As the increasing voltage is applied, the magnitude of the current passing between the electrodes is monitored. It is observed that the current magnitude increases with increasing voltage up to a maximum value, referred to herein as the peak current, and then decreases. In a graphical plot of current versus applied voltage, the peak current is represented as a maximum point in the current/voltage curve. Provided the voltage is applied in a reproducible manner each time, the magnitude of the peak current at the maximum point can be correlated with the strength of the metal processing solution.

As an alternative to measuring the magnitude of the peak current, the current may be monitored as a function of time, again provided the voltage is applied each time in a reproducible manner. The time lapse up to the point of maximum current may then likewise be related to the strength of the metal processing solution.

The present invention is employed by first making a series of measurements on a set of standard solutions of known strengths and correlating the observed peak currents with actual, known solution strengths. The actual strengths of such solutions are normally determined by conventional methods of the types mentioned above. The strength of an unknown solution is then determined empirically by correlating the peak current obtained for the unknown solution with the data for the standard solutions.

BRIEF DESCRIPTION OF THE DRAWINGS

A better understanding of the present invention can be derived by reading the ensuing specification in conjunction with the accompanying drawings, wherein.

DESCRIPTION OF THE PREFERRED EMBODIMENT

The present invention is effective to determine the relative strength of metal processing solutions, and particularly those metal processing solutions that involve an oxidation/reduction reaction with a metal in contact with the solution. Typical metal processing solutions involving oxidation/reduction reactions include electroless plating solutions, such as electroless nickel plating solutions and electroless copper plating solutions, and etching solutions, such as aluminum etching solutions normally employed to remove aluminum oxide layers from aluminum articles.

Electroless nickel plating solutions, for example, contain reactants including a reducing agent such as a hypophosphite, organic acid buffers, chelating agents and nickel ions. The hypophosphite reacts catalytically with a metal substrate surface to produce both hydrogen and hydride ions. The hydride ions are produced on the surface of the metal immersed in the solution, rendering the metal electrically negative relative to the solution. Nickel cations in solution are thus reduced to metallic nickel at the surface of the metal article, thereby forming a deposit of nickel plating on the metal article. Since the plated nickel also acts as a catalyst for the hypophosphite reaction, the plating reaction continues to plate nickel until the solution is exhausted, that is, until all of the nickel ions in the solution are reduced to metallic nickel. One of ordinary skill will readily recognize that as the concentrations of nickel ions and other reactants in the solution decrease, the plating rate will also decrease. In practice, the solution is deemed to be spent when the strength of the solution, as measured by its plating rate on a test sample of metal, is reduced below a predetermined value referred to as the specification limit of the solution. When the specification limit has been reached, the solution is replenished or replaced.

Electroless copper plating solutions are similar in chemistry to electroless nickel plating solutions and similarly, contain organic reducing agents, buffers, chelating agents and copper ions. Similarly, as the reactants are depleted from the solution as copper is plated onto a metal immersed in the solution, the electroless copper solution becomes spent, that is, the copper ions and other reactants become depleted to the point where it is uneconomical to continue using the solution.

Although the reaction chemistry of etching solutions is different from that of the electroless plating solutions, an oxidation/reduction reaction is still employed. A typical aluminum "deoxidizing" solution, for example, comprises nitric acid, chromic acid and a fluoride catalyst. When the reactants in the etching solution are depleted, again, the solution is spent and can no longer be economically employed for commercial purposes.

A typical electroless nickel plating solution upon which the methods and apparatus of the present invention are operative is available from the Shipley Company, Inc. of Newton, Mass. under the tradename Niposit 65. An electroless copper plating solution can also be obtained from the Shipley Company under the tradename Cuposit. A typical aluminum deoxidizing solution such as that described above is available from AmChem Products, Inc. of Ambler, Pa. under the tradename "AmChem 6-16".

In accordance with the present invention, the strength of an electroless nickel plating solution as described above can be determined. If all other factors are kept constant, the plating rate of a solution varies according to the degree to which a given reactive ionic species in solution has been depleted relative to a common reference point such as the concentration of the ionic species in a fresh, unused solution. By determining the plating rate, an operator of an electroless plating operation, for example, can readily determine when to add makeup components to the plating solution or to discard the solution, as the case may be. As will be realized upon reading further, the methods and apparatus of the present invention quickly, accurately and reproducibly provide the operator with the plating rate of the solution. Furthermore, little training or expertise is required to use the apparatus and perform the methods of the invention.

Figure 1:
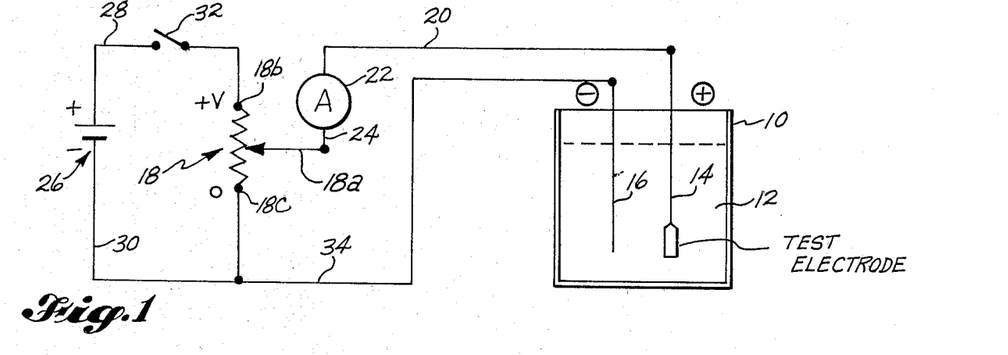
FIG. 1 is a schematic diagram of a very simple circuit that can be used to perform the method of the present invention.

Referring to FIG. 1, a container 10 is filled, for example, with an electroless nickel plating solution 12 such as that described above. Two electrodes 14 and 16 are positioned in spaced relationship and are immersed in the solution 12. The electrode 14 is the positive electrode and will be referred to as the test electrode. The other electrode 16 is immersed in the solution for purposes of setting up an electrical field that changes the potential of the positive test electrode relative to the solution, and will hereafter be referred to as the power electrode. Preferably, each of the electrodes 14 and 16 are made of nickel, or at least plated with nickel, in the case of an electroless nickel plating solution. The positive test electrode 14 is coupled to one terminal of an ammeter 22 by a lead 20 while a second lead 24 couples the other terminal of the ammeter 22 to the slider 18a of a potentiometer 18. The terminals 18b and 18c of the potentiometer 18 are coupled in series to the terminals of a direct current energy source, such as battery 26, by leads 28 and 30, respectively. A swtich 32 is interposed in series within lead 28 for purposes of selectively controlling the current flowing through the potentiometer 18. The negative power electrode 16 is coupled via lead 34 to lead 30 and thus to the negative side of the battery 26 and to the terminal 18c of the potentiometer.

In operation, the slider 18a of the potentiometer 18 is first positioned adjacent the negative terminal 18c of the potentiometer. Thus, both electrodes 14 and 16 are at the same potential and no current flows through the solution 12. The method of the present invention is initiated by closing the switch 32 and thereafter applying an increasing voltage across the electrodes 14 and 16 by moving the slider 18a from its position adjacent terminal 18c toward the positive terminal 18b of the potentiometer. Application of the increasing voltage initially causes an increasing current to flow through the solution 12 between the electrodes 14 and 16.

Figure 2:
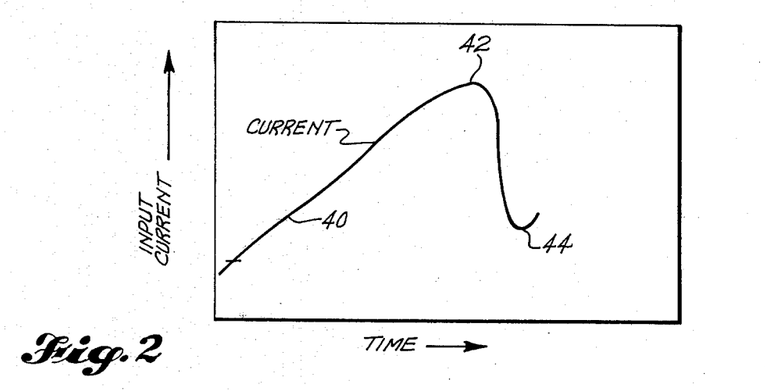
FIG. 2 is a graph of current with respect to time as the voltage is increased across the electrodes shown in FIG. 1 in accordance with the present invention.

Referring to FIG. 2, a graph of current between the electrodes 14 and 16 is shown with respect to time as the increasing voltage is applied to the electrodes. For purposes of the graph, it is assumed that the voltage applied to the electrodes is increased at a constant rate from zero to a finite value of several volts. As the voltage is increased, the current flowing between the electrodes is read from ammeter 22. As indicated by curve 40, the current increases with respect to time (increasing voltage) first at a generally linear rate. The rate of increase of the current then begins to decrease until the magnitude of the current reaches a maximum value at a peak in the current-time curve indicated by reference numeral 42. The maximum value of the current is referred to herein as the peak current. At the peak current, the magnitude of the current begins decreasing even though the voltage applied to the electrodes continues to increase. The magnitude of the peak current is indicative of the strength of a processing solution, such as the plating rate of an electroless nickel plating solution. When the voltage applied to the electrodes is increased at a constant rate, for example at 40 millivolts per second, and is reproducibly increased from a predetermined minimum to a predetermined maximum, the reproducibility of the curve shown in FIG. 2 is quite high. For example, when successive peak current determinations are made on an electroless nickel plating solution having the same temperature, pH and nickel ion concentration and the voltage is increased at a constant rate from 0 to 250 millivolts, the peak current point 42 will occur at substantially the same current magnitude, provided of course that electrical circuit parameters are maintained constant.

The magnitude of the peak current will vary along with a variation in the chemical activity parameters of a given solution. For example, the magnitude of the peak current will increase or decrease, respectively, with an increase or decrease in the concentration of an active ion, such as nickel ion or hypophosphite ion, and will increase or decrease, respectively, with an increase or decrease in temperature, or will increase or decrease with an increase or decrease in pH. The variation in the magnitude of the peak current can thus provide an indication of the relative strength of the processing solution. Thus the present invention can be employed for process control, for example, to periodically check the plating rate of an electroless nickel plating solution to determine when that solution should be replaced or replenished. By using the method and apparatus of the present invention, a substantial amount of time that has heretofore been required for such process control determinations can be eliminated.

It can generally be said that as an increasing voltage is applied across the test and power electrodes in accordance with the invention, the current is monitored to determine the point at which the generally increasing current begins to decrease. With apparatus constructed in accordance with the present invention to provide a uniformly reproducible sweep rate, that is, an apparatus constructed to increase the voltage at a constant and uniformly reproducible rate, the current need not be monitored directly, but instead the time from the beginning of the application of the increasing voltage to the point where the current begins to decrease can be monitored and recorded rather than the absolute magnitude of the current. Accordingly, apparatus can be constructed in accordance with the present invention that provides a value at the peak current in either units of current or units of time. It is to be understood, however, that whether time or current magnitude is the recorded value, the current is still the dependent variable being monitored.

As stated above, the magnitude of the peak current will vary significantly with each one of a number of independent solution variables, including: concentration of each of the active ionic species; temperature of the solution; and pH of the solution. The magnitude of the changes will be illustrated in the following examples. In practice, two of the variables, pH and temperature, are essentially constant, and the remaining variables vary continuously in a consistent manner as the solution becomes depleted. For example, in an operational processing solution such as an electroless nickel plating solution, the solution temperature is normally maintained very close to 90° C. Moreover, the pH of the solution does not vary significantly from the desired pH of 5.0 as the nickel is depleted from the solution. Thus, in practice, two of the independent variables, pH and temperature, remain essentially fixed. Consequently, in practice, the current magnitude at the current peak varies substantially only with a change in nickel or hypophosphite concentration. The same holds true for the other processing solutions, such as the electroless copper plating solutions and etching solutions discussed above.

In order to relate the peak current magnitude to an absolute value of, for example, nickel plating rate, it is first necessary to run a series of peak current magnitude determinations on solutions of known but varying nickel plating rates at the pH and temperature corresponding to pH and temperature of the plating solution of unknown strength. The peak current magnitudes of the known solutions can then be related to their respective plating rates in graphic or tabular form. Thereafter, when it is desired to determine the absolute nickel plating rate of a plating solution, an operator merely immerses the electrodes of an apparatus embodying the circuit described above in the solution of unknown plating rate and monitors the current to determine the current magnitude at the peak point. The operator can then compare the current magnitude reading obtained with the graph or table previously prepared to find the absolute value of the nickel plating rate.

The current magnitude at the peak current will also vary with changes in two physical parameters associated with the electronic circuit used to apply the increasing voltage and to provide the current magnitude reading. These physical parameters are the spacing of the electrodes and the surface area of the test electrode 14. Variations in electrode spacing will vary the impedance between the electrodes and thus the peak current. A variation in the test electrode surface area will alter the active plating or etching area and thus alter the potential magnitude required to reach the peak current point. Accordingly, it is most preferred that the surface area of the test electrode 14 be relatively small, on the order of one square centimeter, and that the electrode spacing be on the order of one centimeter.

Additionally, one of ordinary skill will realize upon reading the specification that at least one and preferably both of the electrodes must be composed of a material that is reactive with or acted upon by a given solution being tested. For example, the electrodes used to test a nickel plating solution are preferably each composed of nickel or a nickel-plated conductive material. Likewise, the electrodes employed for a copper plating solution are preferably each composed of copper; and the electrodes employed for an aluminum etching solution are preferably each composed of aluminum. In practice, it is found that the method works satisfactorily so long as at least the test electrode 14 is composed of a metal of the type plated from a plating solution or a metal that is etched by an etching solution.

EXAMPLES

The following Examples are intended to be illustrative of and to teach one of ordinary skill how to make and use of the present invention. They are not in any way intended to limit the scope of Letters Patent granted hereon.

Figure 3:
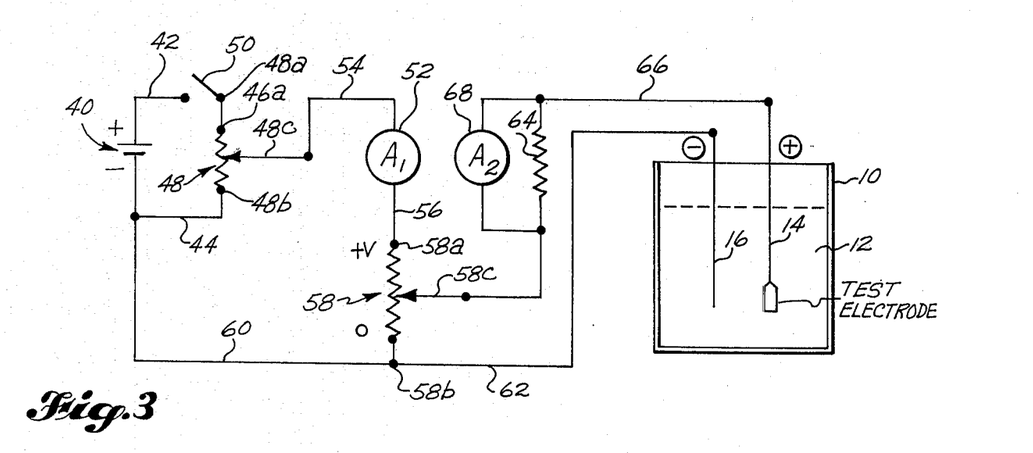
FIG. 3 is a schematic diagram of a circuit constructed in accordance with the present invention employed to provide the results set forth in the Examples.

For purposes of the following Examples, a circuit of the type illustrated in FIG. 3 was employed. The circuit illustrated in FIG. 1 could as well have been employed; however, it was desired to preset the voltage applied to the potentiometer used to apply the increasing voltage to the test and power electrodes. Thus the somewhat modified circuit illustrated in FIG. 3 was employed. The terminals of a DC power source, battery 40, are coupled via leads 42 and 44 to the first and second terminals 48$a$ and 48$b$ of a first potentiometer 48. A manually operated ON/OFF switch 50 is interposed in series with lead 42. The slider 48$c$ of the first potentiometer 48 is coupled to one terminal of a first ammeter 52 by a lead 54. The first ammeter is employed merely to provide a means to check the battery voltage when the switch 50 is closed. The second terminal of the ammeter 52 is connected by lead 56 to a first terminal 58$a$ of a second potentiometer 58. The second terminal 58$b$ of the second potentiometer 58 is connected by lead 60 to lead 44, thus coupling the second terminal 58$b$ of the second potentiometer to the second terminal 48$b$ of the first potentiometer and the negative terminal of the battery 40. The second terminal 58$b$ of the second potentiometer is also coupled to the power electrode 16 by lead 62. The slider 58$c$ of the second potentiometer 58 is coupled to the test electrode 14 through a second ammeter 68 having a current shunt 64 for determining the range of the ammeter. The peak current reading is taken from the second ammeter 68.

The circuit of FIG. 3 is calibrated by closing the switch 50 and adjusting the first potentiometer 48 to provide a desired maximum voltage that can be applied through the second potentiometer 58 when the electrodes 14 and 16 are immersed in the solution 12 being tested. Once the desired maximum voltage is set, the slider 58c of the second potentiometer is positioned adjacent terminal 58b of potentiometer 58 so that both electrodes are at the same potential, thus initially allowing no current to flow through the electrodes 14 and 16 when they are immersed in the solution. Once the test electrodes 14 and 16 are immersed in the solution 12 to be tested, the slider 58c is manually operated to apply an increasing voltage across electrodes 14 and 16 in the solution in a manner similar to the operation of potentiometer 18 described in connection with FIG. 1.

EXAMPLE 1

Approximately 20 ml. of a fresh electroless nickel solution was placed in a beaker. The fresh electroless nickel plating solution, Niposit 65 identified above, contained about 7 to 8 grams per liter of nickel and approximately 23 grams per liter of ammonium hypophosphite. The pH of the fresh solution was approximately 4.8. The solution was heated to about 99° C. and was maintained at that temperature throughout the remainder of the test. The nickel ion concentration in the solution was gradually depleted by successively plating ½ inch (1.27 cm) square steel panels for three minutes each. The amount of nickel depleted from the solution and plated onto each panel was determined by weighing each panel before and after it was immersed in the solution, and finding the difference between the two weights. The amount of nickel deposited in each three minute period thus gives a measure of the plating rate, or strength, of the solution after each successive use of the solution.

After each panel was plated, an apparatus constructed in accordance with with the present invention and employing a circuit like that shown in FIG. 3 was employed to determine the magnitude of the peak current. The magnitude of the peak current as displayed on the second ammeter 68 was recorded after each panel was plated. The values of the components of the circuit were, referring to FIG. 3, potentiometer 48, 50 Kilohms; potentiometer 58, 50 Kilohms; resistor 64, 2 ohms; scale on ammeter 52, 0–50 milliamps; scale on ammeter 68, 0–150 microamps. The first potentiometer 48 was set to provide a maximum voltage across the terminals of ammeter 52 of about 1.5 volts. The electrodes when immersed in the plating solution were spaced apart by about 1 centimeter. The conductive portion of the test electrode immersed in the solution had a total surface area of about 1 square centimeter. Throughout the series of tests, the temperature of the electroless nickel plating solution was maintained constant at 99° C. The pH of the solution was maintained at a constant value of 4.8. A rate of voltage increase applied from potentiometer 58 to the electrodes was approximately 40 millivolts per second for each of the several peak current determinations.

Figure 4:
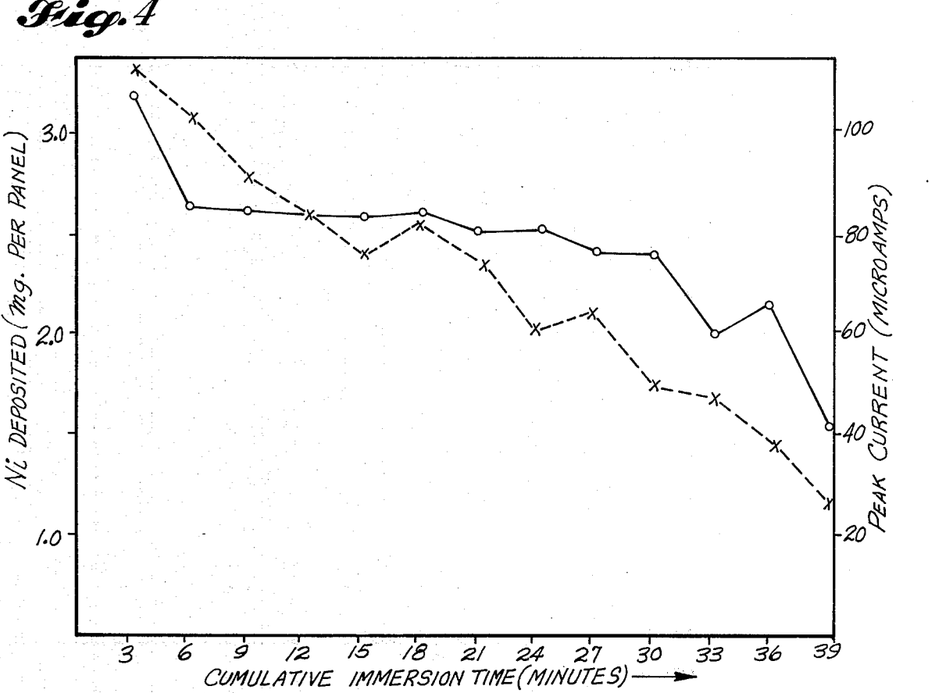
FIG. 4 is a graph of the amount of nickel deposited from an electroless nickel plating solution onto a test specimen along with a graph of the magnitude of the peak current at the maximum current point determined in accordance with the present invention, each plotted versus the time the specimen was immersed in the solution.

The amounts of nickel plated on each successive steel panel were recorded and were plotted on the graph of FIG. 4 versus cumulative immersion time for the test panels and are represented by the data points "0". It should be apparent to one skilled in the art that the graph plotting the amount of nickel deposited in each interval as a function of cumulative immersion time is graphically equivalent to a plot of the plating rate as a function of solution depletion. After each panel was plated, the peak current magnitude was read from the second ammeter 68 and was recorded and plotted on the graph of FIG. 4 versus cumulative immersion time for the test panels. The peak current values are represented by the data points "x".

As is apparent from FIG. 4, the nickel plating rate, as measured by the amount of nickel plated onto each steel panel in each successive interval, progressively decreased as successive panels were plated. The plating rate was initially in excess of 6 mg per square inch (0.93 mg per square centimeter). Beginning with the second test panel, the plating rate leveled off to about 5 mg per square inch (0.775 mg per sq. cm.) and remained substantially constant, although decreasing slightly, through the tenth test panel. Thereafter, on the eleventh through thirteenth test panels, the plating rate fell quickly, indicating that the plating solution was substantially depleted. At the same time the peak current reading taken after plating each successive panel indicated an average downward trend. The variations of the actual peak current magnitude readings from a smooth line through the data point can be accounted for by variations in the rate of increase of the voltage applied to the electrodes from a desired constant rate. The variations in the rate of increase occurred because the potentiometer 58 was operated by hand, and thus was not turned at exactly the same speed for each test run.

For a given electroless nickel plating solution of unknown strength, one of ordinary skill will readily realize that the graph of FIG. 4 can be utilized to determine the absolute plating rate of such solution, provided the solution to be tested is at approximately the same temperature and pH as that of the test solution employed to generate the results depicted in FIG. 4.

EXAMPLE II

Figure 5A:
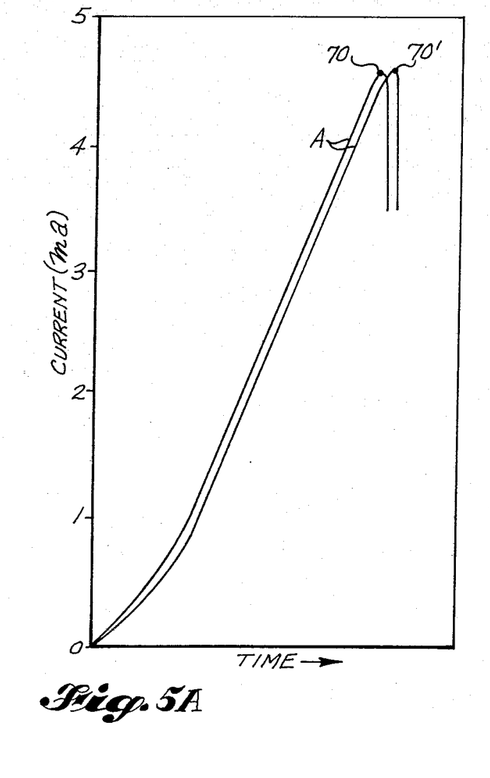
FIGS. 5A, 5B and 5C are graphs of current versus time illustrating the maximum current point determined in accordance with the present invention for a fresh metal processing solution, a partially depleted metal processing solution, and a depleted metal processing solution.

To illustrate the reproducibility of the peak current reading obtained in accordance with the present invention, a series of duplicate runs were made on electroless nickel plating solutions having different nickel concentrations. Again, a fresh electroless nickel plating solution, Niposit 65, was first employed. The fresh solution contained 8.0 grams per liter of nickel and had a pH of 4.8. For all runs in this Example, the pH was maintained at 4.8 while the temperature of the solution was maintained at 99.5° C. The surface area of the portion of the test electrode 14 immersed in the solution was approximately 1 square centimeter. An apparatus embodying the circuit of FIG. 3 was employed to make the tests. A voltage increase rate of approximately 40 millivolts per second was applied to the electrodes with the second potentiometer 68. Because a voltmeter was placed across the electrodes 14 and 16 and because other test equipment was coupled into the circuit, the absolute values of the current readings obtained from ammeter 68 when the inflection point was reached were different from those obtained in the previous Example. An X-Y recorder was coupled in parallel across shunt resistor 64 and was set to trace current versus time. A first set of duplicate tests was made on the fresh solution identified as Solution A. The two successive graphs plotted by the recorder are reproduced in FIG. 5A and identified as graphs A. The values on the ordinate correspond approximately to milliamp readings taken from the second ammeter 68. As can be seen, two successive tests on Solution A yielded virtually identical current magnitudes at the identical peak current points 70 and 70'.

Figure 5B:
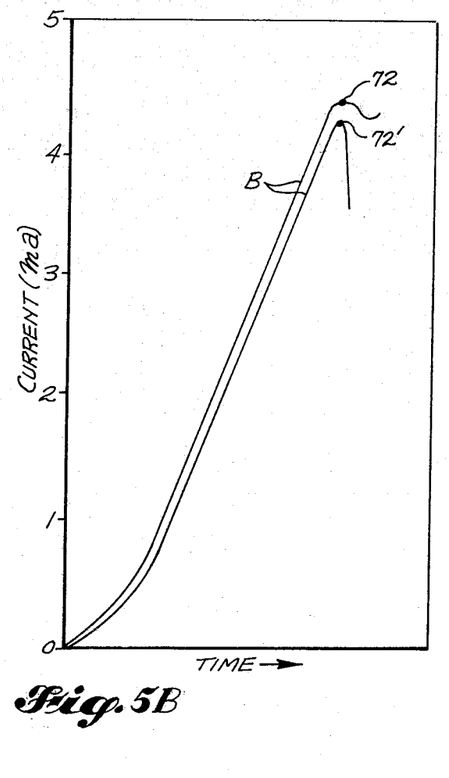

A second set of duplicate tests was made on a second solution identified as Solution B. Solution B was prepared by diluting Solution A with water so that it contained 6.0 grams per liter of nickel, as well as correspondingly less hypophosphite. The graphs identified by the letter B in FIG. 5B are reproductions of the graphs recorded on the X—Y recorder. Again, as can be seen, the peak current points 72 and 72' are substantially the same, indicating good reproducibility of results. Again, the slight discrepancy in the peak current readings at points 72 and 72' on the B graphs were caused primarily by a slight variation in the rate at which the voltage applied to the electrodes was increased.

Figure 5C:
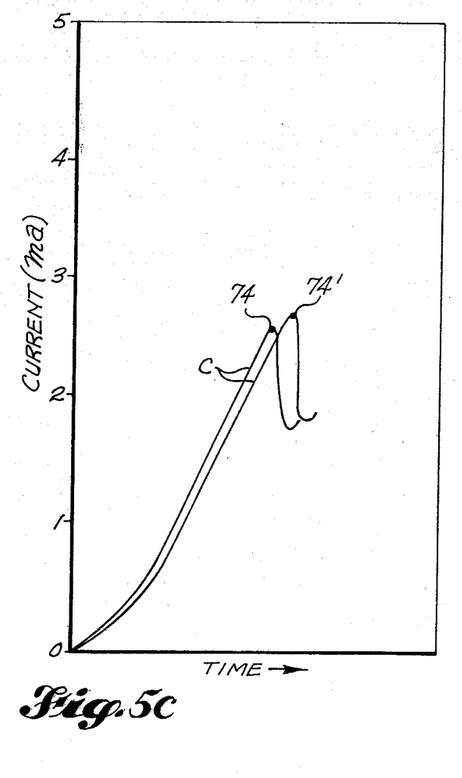

A third set of duplicate tests were conducted on a solution identified as Solution C. Solution C comprised one part of Solution B and one part of water. Two successive graphs obtained from the X—Y recorder while conducting tests on Solution C are identified by the letter C and are reproduced in FIG. 5C. As can be seen, the current magnitudes at the peak points 74 and 74' again are substantially the same, thus showing that the reproducibility of the results utilizing the methods and apparatus of the present invention is excellent.

EXAMPLE III

Figure 6A:
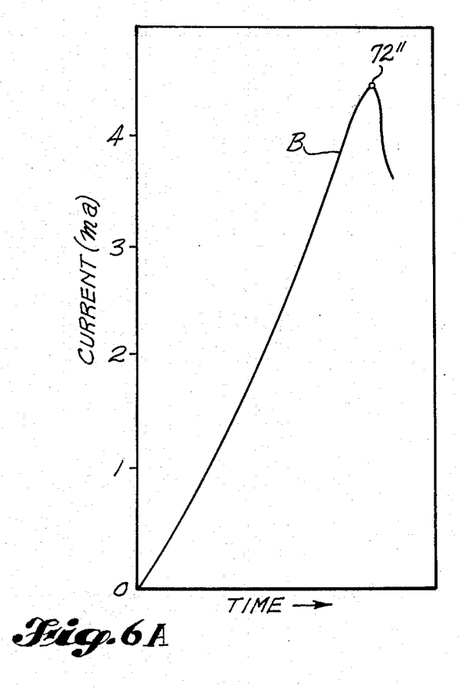
FIGS. 6A and 6B are graphs similar to those shown in FIG. 5 for other metal processing solutions.
Figure 6B:
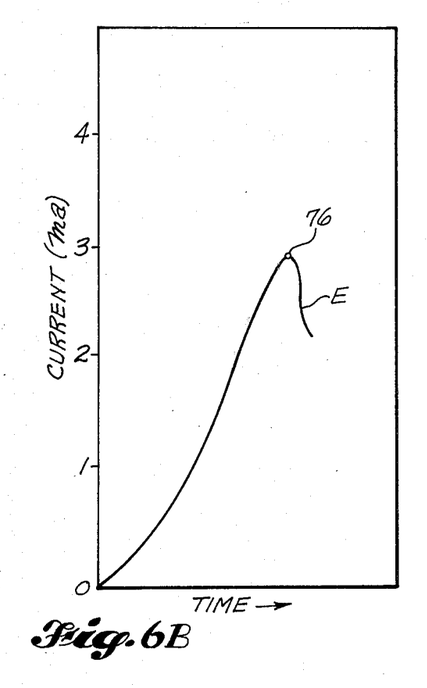

The procedure of Example II was repeated on Solution B of Example II. An X—Y recorder plot of the graph of current versus time is reproduced in FIG. 6A and indicated by the letter B. As can be seen, the peak current magnitude at the point 72" on graph B of FIG. 6A is virtually the same as that shown for Solution B in FIG. 5B. A Solution E was then made from Solution B by depositing nickel on a steel plate. A ½ inch square (3.2 square centimeter) steel plate was first weighed and then immersed in 250 ml of Solution B. When withdrawn from the solution, the steel plate and nickel plated thereon were weighed. By finding the difference in the weights, it was found that 0.0845 grams of nickel had been plated on the steel plate. The peak current test in accordance with the present invention was then conducted on Solution E to determine the peak current magnitude for Solution E. An X—Y recorder plot of the graph of current versus time is reproduced as graph E of FIG. 6B. The point 76 for Solution E occurred at a substantially lower current magnitude than the corresponding point 72" for Solution B, again illustrating that the magnitude of the peak current provides a relative indication of the strength of the plating solution.

EXAMPLE IV

To illustrate the variation in the magnitude of the peak current as a function of various factors, a series of tests were made on a fresh, electroless nickel plating solution, Niposit 65, wherein temperature, total reactant concentration and pH were each independently varied, while the other two were maintained constant. Graphs 78, 80 and 82 of FIG. 7 depict, respectively, variations in temperature, solution concentration and pH, versus the peak current magnitude.

For the temperature graph 78, the abscissa represents the peak current magnitude in milliamps while the values on the left hand ordinate represent the temperature in degrees Celsius of a fresh electroless nickel plating solution having a pH held constant at 4.8, and constant reactant concentrations corresponding to a nickel concentration held constant at approximately 8 grams per liter. The fresh electroless nickel solution was first heated to about 85° C. and the peak current magnitude reading taken in accordance with the present invention. This value was plotted on the coordinate system of FIG. 7. The temperature of the solution was then raised in approximately 1.5° C. increments and new peak current readings taken and plotted on FIG. 7. These values are represented by the "0" data points on FIG. 7 and are normalized with the graph 78. As can be seen by reference to FIG. 7, the magnitude of the peak current rises with temperature.

Figure 7:
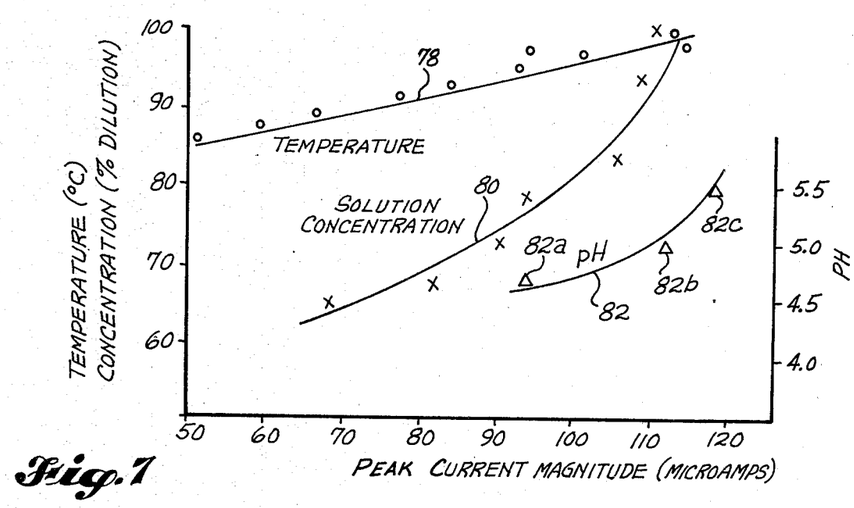
FIG. 7 is a plurality of graphs of the peak current magnitude determined in accordance with the present invention at varying temperatures, solution concentrations, and pH of a particular type of metal processing solution.

For the solution concentration graph 80, data points "x" were plotted on the coordinate system of FIG. 7. For the solution concentration graph 80, the abscissa represents the magnitude of the peak current in milliamps while the left hand ordinate values represent volume percent dilution with water of a fresh solution initially containing approximately 8.0 grams per liter of nickel. The temperature and pH of the solution were maintained constant at about 99° C. and 4.8, respectively, for each of the data points generated. The data point corresponding to 100% on the ordinate indicates that the test solution was a fresh, undiluted electroless nickel plating solution. The data point below at approximately the 93% value on the ordinate indicates that the test solution was approximately 93% by volume fresh electroless solution while the remainder was water. Similarly, the next data point represents a test solution having approximately 82% by weight fresh electroless nickel solution, the balance being water, and so on. As shown by graph 80, the magnitude of the peak current drops rapidly with the dilution of the electroless nickel solution.

To illustrate the variation in the magnitude of the peak current with pH, a fresh electroless nickel solution containing 8.0 grams per liter of nickel was placed in a beaker and heated to a temperature of 99.5° C. The magnitude of the peak current was then determined in accordance with the present invention and plotted on the coordinate system of FIG. 7 while varying the pH and maintaining the temperature constant at about 99.5° C. and the total reactant concentration at a level corresponding to a constant nickel concentration of 8.0 g/l. The right hand ordinate is in pH units while the abscissa again is the peak current magnitude in milliamps. Data point 82a represented by the triangle is for a fresh electroless nickel solution having a pH of 4.8. The pH of the first solution was then adjusted by the addition of ammonium hydroxide to raise the pH of the solution to 5.0. Data point 82b indicates the magnitude of the peak current for the solution having a pH of 5.0. The pH of the solution was again raised by the addition of ammonium hydroxide to about 5.5. Data point 82c represents the magnitude of the peak current for the latter solution. Thus, it can again be seen that given values for any two of the independently variable activity parameters, temperature, total reactant concentration and pH, the third parameter of an electroless nickel solution can be determined by employing the methods and apparatus of the present invention.

EXAMPLE V

Figure 8:
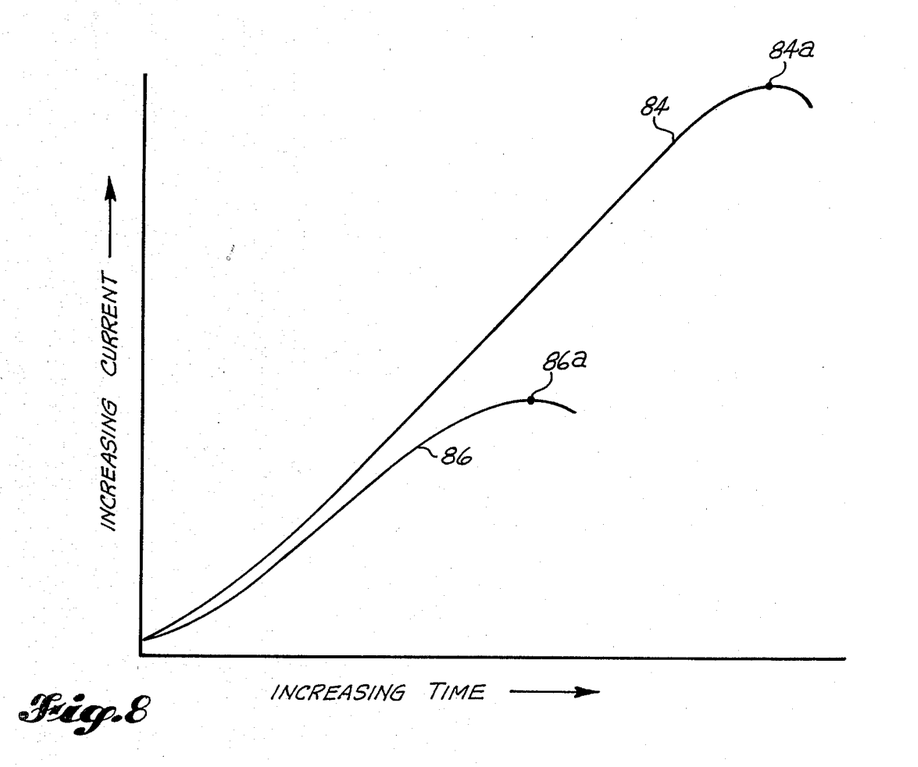
FIG. 8 shows two graphs of current versus time obtained in accordance with the present invention for a fresh aluminum etching solution and a depleted aluminum etching solution.

The method and apparatus of the present invention can be utilized not only on electroless plating solutions but also on etching solutions as discussed above. The Example illustrates the efficacy of the present invention on an aluminum deoxidizing solution containing nitric acid, chromic acid, as well as other reactants. Such a solution is typically used to remove the outer layer of aluminum oxide that commonly forms on metallic aluminum. The aluminum deoxidizing solution used for this Example is a fresh commercial solution made up from materials available from AmChem Products, Inc. of Ambler, Pennsylvania under the tradename Am-Chem 6-16. An aliquot of a fresh solution taken directly from the commercial bath was placed in a beaker. This fresh solution contains about 8.5% by weight of chromic acid and 13.5 oz. per gallon (101 grams/liter) of nitric acid. An apparatus embodying the circuit of FIG. 3 was employed to make peak current magnitude determinations in accordance with the invention. An X—Y recorder was coupled in parallel with shunting resistor 64 and was adjusted to plot current with respect to time. A reproduction of the graph thus obtained is shown in FIG. 8. The new solution is indicated by graph 84. The magnitude of the peak current at point 84a was approximately 9.2 milliamps as read from the second ammeter 68.

A commercially depleted deoxidizing solution was then placed in a beaker. The method and apparatus of the present invention were then used to graph current with respect to time to determine the magnitude of the peak current. The X—Y recorder was set to record current versus time. A reproduction of the graph thus produced is illustrated in FIG. 8 as graph 86. The magnitude of the peak current at the point 86a was approximately 4.2 milliamps. The spent solution contained approximately 9.6 oz./gal. (71.9 g/l) nitric acid and approximately 4% by weight chromic acid. Thus, again, from viewing FIG. 8 along with the accompanying experimental procedure, it can easily be seen that the methods and apparatus of the present invention are effective to determine the relative strength or oxidizing rate of an aluminum deoxidizing solution as well as the strength of electroless plating solutions as described above.

Figure 9:
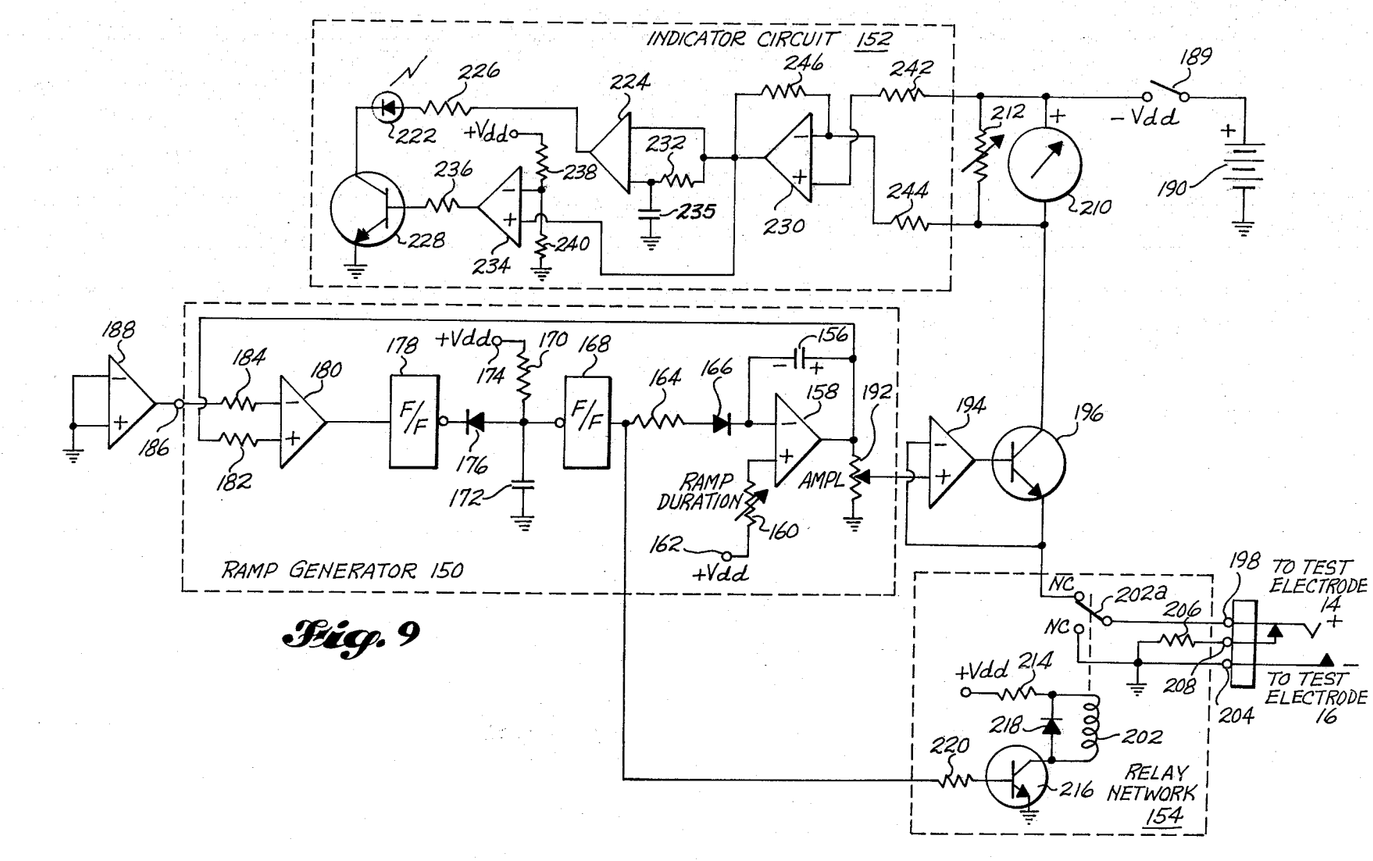
FIG. 9 is a schematic diagram of an electronic circuit that is presently preferred for performing the methods of the present invention.

It is presently preferred to employ a device that can be hand held and easily carried by a technician from one plating or deoxidizing bath to another so that samples of the solution do not have to be carried to the lab for analysis. FIG. 9 schematically depicts a circuit arrangement presently used in one such portable device wherein the depicted arrangement includes: a ramp generator 150 for supplying the linearly increasing voltage to the electrodes 14 and 16; an indicator circuit 152 for providing a distinct visual indication that the current passing between the electrodes 14 and 16 has reached the previously described peak current; and, a relay network 154 for electrically interconnecting the electrodes 14 and 16 prior to the application of each linearly increasing test voltage to ensure that current flows between the test electrodes only during test intervals.

The ramp generator 150 of FIG. 9 is basically a type of voltage time-base generator which can be characterized as a Miller integrator circuit in that a ramp waveform is produced by integrating a step signal. More specifically, the ramp generator 150 includes an integrator circuit having a capacitor 156 interconnected between the inverting input terminal and output terminal of a conventional operational amplifier 158 and having a potentiometer 160 which interconnects the noninverting input terminal of operational amplifier 158 to a terminal 162. As is known in the art, when a positive potential is applied to terminal 162, operational amplifier 158 supplies a constant current to linearly charge capacitor 156 at a rate determined by the RC time constant of potentiometer 160 and amplifier 156. Since the inverting input terminal of operational amplifier 158 is at virtual ground, the voltage at the output terminal thereof linearly increases with the time rate of increase being determined by the setting of potentiometer 160. Since, as shall be described more fully hereinafter, capacitor 156 is rapidly discharged when the linearly increasing voltage reaches a predetermined level, it can be seen that the potentiometer 160 establishes the duration of the test signal and, in situations in which the circuit of FIG. 9 is continuously energized to supply a periodic ramp signal, establishes the frequency of such signal.

To rapidly discharge capacitor 156 at the termination of each linearly increasing test voltage, a resistor 164 and diode 166 are serially interconnected between the inverting input terminal of operational amplifier 158 and the output terminal of a flip-flop 168. The input terminal of flip-flop 168 is connected to the junction between a resistor 170 and a capacitor 172, which are serially interconnected between a terminal 174 and circuit common, and is also connected to the anode of a diode 176 having the cathode thereof connected to the output terminal of a flip-flop 178. The input terminal of flip-flop 178 is connected to the output terminal of an operational amplifier 180 which supplies a positive output signal when the linearly increasing voltage supplied at the output terminal of operational amplifier 158 reaches the previously mentioned predetermined level. In this regard, the noninverting input terminal of operational amplifier 180 is connected to the output terminal of operational amplifier 158 via a resistor 182 and a resistor 184 couples the inverting input terminal of operational amplifier 180 to a reference voltage, $V_r$, which is applied to a terminal 186.

Examining this arrangement, it can be noted that operational amplifier 180 is connected as a difference amplifier and that, since no feedback elements are present, the signal provided by the operational amplifier 180 will be at substantially circuit common potential (zero volts) when the current supplied to the inverting input terminal is greater than the current supplied to the noninverting input terminal thereof. Conversely, the signal supplied by operational amplifier 180 will be at a positive voltage level when the current supplied to the noninverting input terminal exceeds the current supplied to the inverting input terminal. More specifically, as the voltage at the output terminal of operational amplifier 158 linearly increases, the current flowing through resistor 182 increases and the signal provided by operational amplifier 180 rapidly switches from approximately zero volts to a positive level when $I_{R182} - I_{R184} + I_{OS}$ is greater than zero, where the subscripts R182 and R184 respectively denote the current flowing into the noninverting and inverting input terminals of the operational amplifier 180 and $I_{OS}$ denotes the input offset current of operational amplifier 180. Thus, if the reference voltage $V_r$ is established at a suitable level and appropriate resistance values are selected for resistors 182 and 184, operational amplifier 180 will supply a positive voltage to the input terminal of flip-flop 178 when the capacitor 156 is charged to a predetermined value.

For example, in a presently used realization of the depicted circuit, reference voltage $V_r$ is supplied by an operational amplifier 188 having its output terminal connected to the terminal 186 and its inverting and noninverting input terminals connected to circuit common. In this realization, the operational amplifiers 158, 180 and 188 are three of the four amplifiers included in a silicon integrated circuit manufactured by National Semiconductor of Sunnyvale, California and identified as device No. LM3900. Since the amplifiers of this particular device exhibit an input offset current that drives the amplifier output voltage within a few millivolts of the circuit supply voltage whenever equal currents are supplied to the inverting and noninverting input terminals, the operational amplifier 188 supplies a reference voltage $V_r$ which is slightly less than the operating potential applied to terminals 162 and 174. Further, since the operational amplifiers 158, 180 and 188 are portions of a single integrated circuit and exhibit substantially identical performance characteristics, the resistance values of resistors 182 and 184 can be selected so that the maximum voltage provided by the ramp generator 150 is substantially equal to the supply voltage. In particular, in the presently used realization of the depicted circuit, resistors 182 and 184 are respectively 976 Kilohms and 1 Megohm, ±1%. Thus, the current flowing into the noninverting and inverting input terminals of operational amplifier 180 will be substantially equal when the capacitor 156 is charged to a voltage that is slightly less than the circuit supply voltage to cause the signal supplied by operational amplifier 180 to switch between a voltage of approximately zero voltage and a positive voltage level which, in turn, causes flip-flop 178 to change states.

In operation, when the circuit of FIG. 9 is initially energized by closing a switch 189 to connect a battery 190 (or other conventional source of operating potential) to the terminals 162 and 174, there is not initial charge on capacitor 156. Thus, the current flowing into the inverting input terminal of operational amplifier 180 exceeds the current flowing into the noninverting input terminal thereof and operational amplifier 180 supplies a signal of approximately zero volts to the input terminal of flip-flop 178. As is denoted by the small circle at the output terminal of flip-flop 178, a logically low input signal such as zero volts, places the output of flip-flop 178 at a positive voltage level. Thus, as the switch 188 is initially activated, the diode 176 is reverse biased and current flowing through resistor 170 rapidly charges capacitor 172 to a positive voltage that exceeds the output level of flip-flop 178 by approximately one diode drop. As the voltage across capacitor 172 reaches the logical one level of flip-flop 168, flip-flop 168 goes low and, since the inverting input terminal of operational amplifier 158 is at virtual ground, diode 166 is reverse biased.

With the ramp generator 150 thus initialized, current flowing through potentiometer 160 and into the noninverting input terminal of operational amplifier 158 causes capacitor 156 to be linearly charged and supply a linearly increasing voltage at the output terminal of operational amplifier 158.

As previously noted, the maximum voltage that will be obtained by capacitor 156 is established by the reference voltage $V_r$ and the resistance values of resistors 182 and 184, with the time rate of change in the signal supplied by operational amplifier 158 being determined by the RC time constant of capacitor 156 and potentiometer 160. For example, in the previously mentioned realization of the circuit arrangement of FIG. 9, a supply voltage of 8.2 volts is utilized, capacitor 156 has a value of 10 microfarads and potentiometer 160 allows resistance settings within a range of 1 to 2 Megohms.

With these circuit values, the signal provided at the output of the operational amplifier 158 linearly increases between zero volts and approximately 8 volts at a rate ranging between 500 millivolts and 1 volt per second, depending upon the setting of potentiometer 160.

Regardless of the exact circuit values employed, when capacitor 156 is charged to a potential which causes amplifier 180 to supply a positive voltage to the input of flip-flop 178, flip-flop 178 changes states (goes low) to forward bias diode 176. With diode 176 forward biased, flip-flop 168 changes states to supply current to the inverting input terminal of operational amplifier 158 and thereby discharge capacitor 156 at a rate determined by the RC time constant of resistor 164 and capacitor 156. A capacitor 156 discharges, the current into the noninverting input terminal of operational amplifier 180 decreases and the signal supplied to the input terminal of flip-flop 178 becomes approximately zero volts to thereby cause flip-flop 178 to reverse bias diode 176. As diode 176 is reverse biased, capacitor 172 charges through resistor 170 to supply a positive signal level to the input terminal of flip-flop 168. Flip-flop 168 thus changes states to reverse bias the diode 166 to again permit linear charging of capacitor 156. Thus, it can be recognized that as long as the switch 188 is closed, the ramp generator 150 will supply a periodic ramp signal wherein each of the linearly increasing portions of the signal are suitable for determining the inflection current of a plating or deoxidizing solution.

In the arrangement of FIG. 9, a selectable portion of the signal supplied by the ramp generator 150 is applied to the noninverting input terminal of an operational amplifier 194 through the wiper connection of a potentiometer 192 which is connected between the output terminal of operational amplifier 158 and circuit common. The output terminal of operational amplifier 194 is connected to the base electrode of an NPN transistor 196 having the emitter electrode thereof connected to the inverting input terminal of operational amplifier 194 to thereby form an amplifier stage having substantial current gain and very low output impedance.

To couple the ramp signal to the electrodes 14 and 16, the emitter electrode of transistor 196 is connected to a terminal 198 of a conventional jack 200 via the normally closed contacts 202a of a relay 202 and a terminal 204 of jack 200 is connected to circuit common. In this arrangement, electrodes 14 and 16 interconnect with a conventional plug (not shown) which mates with the jack 200 to connect the electrode 14 to circuit common (i.e., jack terminal 204) and connect electrode 16 to the emitter electrode of transistor 196 (through jack terminal 198 and normally closed relay contacts 202a). Further, to provide a circuit load when electrodes 14 and 16 are not connected to the circuit of FIG. 9, a resistor 206 is interconnected between circuit common and a terminal 208 of jack 200. As is schematically indicated, jack 200 electrically connects the resistor 208 to the emitter electrode of transistor 196 only when electrodes 14 and 16 are not connected to the depicted circuit.

To complete the basic test circuit and provide an indication of the current flowing between the electrodes 14 and 16, an ammeter 210 is connected between the circuit supply voltage and the collector electrode of transistor 196 with a potentiometer 212 connected in parallel with ammeter 210 to provide current range selection and meter calibration.

In operation, the linearly increasing voltage supplied by ramp generator 150 is coupled to electrodes 14 and 16 via the amplifier stage that includes operational amplifier 194 and transistor 196. Because of the high current gain of this amplifier stage, substantially all of the current that flows between the test electrodes 14 and 16 flows through ammeter 210 and shunt resistor 212 and the peak current can be observed on ammeter 210.

In view of the above description of ramp generator 150, the operation of the relay network 154 to interconnect the test electrodes 14 and 16 with the ramp generator when the linearly increasing voltage is supplied and to electrically interconnect the electrodes 14 and 16 between linearly increasing portions of the supplied ramp signal can now be understood. In particular, in relay network 154, a resistor 214 and the coil of relay 202 are serially connected between the circuit supply voltage and the collector electrode of an NPN transistor 216 with a suppression diode 218 being connected in parallel with the relay coil. Since the emitter electrode of transistor 216 is connected to circuit common and the base electrode is connected to the output of flip-flop 168 through a resistor 220, it can be recognized that the transistor 216 will energize the relay 202 only when the output of flip-flop 168 is at a positive voltage level. In particular, since the signal supplied by flip-flop 168 is at substantially zero volts while the ramp generator 150 is supplying the linearly increasing voltage, transistor 216 is in a nonconducting state and test electrode 14 is interconnected to the ramp generator 150 via the normally closed relay contacts 202a. However, when flip-flops 178 and 168 are activated to rapidly discharge capacitor 156, the output of flip-flop 168 switches to a positive voltage level and remains at that level for a period of time determined by the transition times of flip-flops 168 and 179 and the RC time constant of resistor 170 and capacitor 172. Thus, transistor 216 energizes relay 202 for a brief period of time between each linearly increasing portion of the signal supplied by the ramp generator 150. Since the normally closed terminal of the relay contacts 202a is connected to circuit common, relay network 154 thus operates to electrically interconnect the electrodes 14 and 16 between linearly increasing test voltages and ensures that there is zero electrical potential between the electrodes 14 and 16 as each test begins.

In view of the circut diagram of FIG. 9 and the above description, those skilled in the art will note that although flip-flops 168 and 178 have been included in the ramp generator 150, these components function to provide a signal of sufficient duration to activate the relay 202. That is, although the ramp generator 150 will supply a periodic ramp signal when the output terminal of operational amplifier 180 is directly connected to the resistor 164, such a configuration would not operate the relay 202. Further, those skilled in the art will recognize that a large number of commercially available logic circuits can be utilized as flip-flops 168 and 178. For example, in the previously mentioned realization of the circuit of FIG. 9, the two Schmitt trigger circuits contained in a silicon integrated circuit that is identified as a 74C14 and manufactured by National Semiconductor of Sunnyvale, California, are utilized.

To provide an easily discernible indication when the peak current is attained, the indicator circuit 152 of FIG. 9 includes a light emitting diode (LED) 222 having the anode thereof connected to the output terminal of an operational amplifier 224 via a current limiting resistor 226 and the cathode thereof connected to circuit common through the collector-emitter path of an NPN transistor switch 228. In this arrangement, operational amplifier 224 detects the peak circuit by detecting the change in slope in the current flowing through the ammeter 210 to emergize LED 222 and transistor 228 prevents LED 222 from providing a visual indication during discharge of capacitor 158 (i.e., during the short time interval between successive linearly rising portions of the signal supplied to electrodes 14 and 16).

More specifically, the output terminal of an operational amplifier 230, which supplies a signal representative of the current flowing through the ammeter 210, is directly connected to the inverting input terminal of operational amplifier 224 and the noninverting input terminal of operational amplifier 224 is connected to the junction between a resistor 232 and capacitor 235 that are serially interconnected between the output terminal of operational amplifier 230 and circuit common. Further, the output terminal of operational amplifier 230 is connected to the noninverting input terminal of an operational amplifier 234 having the output terminal thereof connected to the base electrode of transistor 228 via a resistor 236 and the inverting input terminal of operational amplifier 228 via a resistor 236 and the inverting input terminal of operational amplifier 234 is connected to the junction between resistors 238 and 240, which form a voltage divider connected between the circuit supply voltage and circuit common. To complete indicator circuit 152, the noninverting input and inverting input terminals of operational amplifier 230 are connected to the positive and negative terminals of ammeter 210 via resistors 242 and 244 and a feedback resistor 246 is connected between the inverting input terminal and output terminal of operational amplifier 230.

To provide optimum operation of the indicator circuit 152, resistors 242 and 244 are selected so that operational amplifier 230 provides an output level of substantially zero volts when no current flows through ammeter 210, i.e., at the initiation of each linearly increasing test voltage. Further, resistors 238 and 240 are selected so that operational amplifier 234 maintains transistor 228 in the nonconducting state during the initial portion of the linearly increasing test voltage. That is, resistors 238 and 240 bias operational amplifier 234 so that transistor 228 conducts only after the current through ammeter 210 attains a predetermined value. Generally speaking, satisfactory results have been achieved when this predetermined current corresponds to approximately 3-4 percent of the voltage swing of ramp generator 150. In addition, resistor 232 and capacitor 235, which primarily control the sensitivity of the indicator circuit 152, are selected to exhibit a RC time constant that causes the inverting and noninverting input terminals of operational amplifier 224 to remain at substantially the same potential as the current through ammeter 210 increases while simultaneously maintaining the noninverting input terminal of the operational amplifier 224 at a relatively constant potential when the current through the ammeter 210 decreases (i.e., when the peak current is reached).

In the previously mentioned and presently used realization of the circuit of FIG. 9, two of the three amplifiers included in a silicon integrated circuit denoted as a LM324, available from Texas Instruments of Dallas, Texas, are utilized as operational amplifiers 224 and 234; the fourth amplifier of the previously mentioned LM3900 integrated circuit is utilized as operational amplifier 230; and, a 2N2222 is utilized as transistor 228. In this circuit realization, resistors 232, 238, 240, 242 and 244 are 20 kilohms, 22 kilohms, 1 kilohm, 820 kilohms and 800 kilohms, respectively, while capacitor 235 has a value of 0.1 microfarads.

The operation of indicator circuit 154 can be understood in view of the above described circuit arrangement and the operation of the invention as described relative to FIGS. 1 and 3. In particular, as ramp generator 150 begins to supply a linearly increasing voltage to electrodes 14 and 16, current through ammeter 210 begins to increase, which, in turn, causes operational amplifier 230 to supply a positive output voltage representative of the magnitude of the current flowing between electrodes 14 and 16. When the voltage supplied by operational amplifier 230 causes the potential at the inverting input terminal of operational amplifier 234 to rise above the potential established at the inverting input terminal by resistors 238 and 240, operational amplifier 234 drives the base electrode of transistor 228 to a positive level which causes transistor 228 to conduct and provide a current path between the cathode of LED 222 and circuit common. During this initial portion of the test sequence and during subsequent portions in which the current through ammeter 210 continues to increase, capacitor 235 is charged through resistor 232 at a rate which maintains the noninverting and inverting input terminals of operational amplifier 224 close enough in potential so that operational amplifier 224 supplies little or no output current and LED 222 remains de-energized. As the peak current is reached, the current through ammeter 210 decreases and the potential supplied to the inverting input terminal of operational amplifier 224 by operational amplifier 230 decreases. Since the rate at which current increases before the peak current is reached is substantially less than the rate of current decrease after the peak current is reached, capacitor 235 holds the noninverting input terminal of operational amplifier 224 at a potential that exceeds the potential coupled to the inverting input terminal thereof by operational amplifier 230. Thus, operational amplifier 224 supplies current that energizes the LED 222 and an indication of the peak current is effected.

Those skilled in the art will recognize that LED 222 would supply the above described indication of the peak current if the cathode of the LED 222 were connected directly to circuit common and the portion of the circuit which includes operational amplifier 234 and transistor 228 were eliminated. However, such an arrangement would also permit LED 222 to be momentarily energized at the termination of each linearly increasing test voltage, i.e., as the capacitor 156 is discharged. Such energizaton of LED 222 would present a drawback in that, should the operator of the equipment set the potentiometer 192 so that the linearly increasing test voltage is not sufficient to attain the peak current energization of LED 222 at the termination of each linearly increasing portion of the test voltage could erroneously be interpreted as an indication of the peak current. Further, if the voltage beween electrodes 14 and 16 continues to increase after the peak current has been attained, the current first decreases and then again begins to increase. Thus, if the indicator circuit 152 did not include means for preventing energization of LED 222 during the discharge of capacitor 156, LED 222 would be energized as the peak current was reached, would deenergize as the current began to increase again, and would be energized for a second time at the end of each linearly increasing portion of the ramp signal provided by the ramp generator 150.

The preferred circuit is encased in a suitable housing (not shown) that can be held in an operator's hand. The ammeter and LED are, of course, visible through the housing. The electrodes 14 and 16 protrude from the housing. The test electrode is composed of nickel plated steel or copper, in the case of an electroless nickel plating solution to be monitored, and extends from the housing in the form of a rod having a diameter of about 0.25 centimeter. The test electrode 14 terminates in a pad having a total surface area of 1 square centimeter. The power electrode 16 is a rod having a diameter of 0.25 centimeter, is generally oriented parallel to the test electrode, and is separated from the test electrode by a distance of 1 centimeter.

In operation of the preferred circuit and apparatus, the electrodes 14 and 16 are immersed in the solution to be tested. The operator energizes the circuit by closing switch 189 and visually noting the current reading display on the ammeter. When the LED is energized, indicating that the peak current has been reached, the operator immediately reads the current value displayed on the ammeter and records it. By reference to an appropriate graph or chart previously prepared, the strength of the solution can thus be determined.

The present invention has been disclosed in relation to several embodiments. One of ordinary skill after reading the foregoing specification will be able to effect various changes, substitutions of equivalents and other changes without departing from the broad concepts imparted herein. For example, one of ordinary skill will readily realize that the methods and apparatus of the present invention can readily be employed with automatic process control systems to provide input data for constantly monitoring the strength of a process solution. Such automatic process control systems can even provide for the automatic addition of make-up components to a spent or partially depleted solution. It is therefore intended that the scope of protection granted by Letters Patent hereon be limited only by the definition contained in the appended claims and equivalents thereof.

The embodiments of the invention in which an exclusive property or privilege is claimed are defined as follows:

1. A method of measuring the etching rate of a chemical etching solution with respect to a predetermined metal susceptible to etching by said solution, comprising the steps of:
   (a) immersing a pair of spaced electrodes in a chemical etching solution capable of oxidizing said predetermined metal in its native form to an oxidized ionic species in solution, at least one of said electrodes being composed of said predetermined metal susceptible to etching by said etching solution;
   (b) applying an increasing electrical potential across said spaced electrodes to thereby produce an electric current through said solution between said electrodes; and
   (c) monitoring said current to determine the magnitude of the peak current at the point at which said current first begins to decrease as said increasing potential is applied.

2. The method of claim 1 wherein both of said electrodes are composed of said predetermined metal susceptible to etching by said solution.

3. The method of claim 2 wherein said electric potential is increased from zero at a linear rate of increase.

4. The method of claim 1 wherein the polarity of said one electrode composed of said predetermined metal susceptible to etching by said etching solution is positive when said electrical potential is being applied across said electrodes.

5. The method of claim 1, 4, or 3 further comprising the step of correlating the magnitude of said peak current with the magnitudes of peak currents obtained for standard solutions of known absolute etching rates to thereby determine the absolute etching rate of said etching solution.

6. The method defined in claim 1 wherein said chemical etching solution is an aluminum deoxidizing solution.

7. A method of determining the plating rate of a catalytic electroless metal plating solution comprising the steps of:

(a) immersing a pair of spaced electrodes in a catalytic electroless plating solution, at least one of said electrodes being composed of a metal susceptible to plating by said electroless plating solution;

(b) applying an increasing electric potential across said spaced electrodes to thereby produce a current through said solution between said electrodes; and (c) monitoring said current to determine the magnitude of the peak current at the point at which said current first begins to decrease as said increasing potential is applied.

8. The method of claim 7 wherein both of said electrodes are composed of a metal susceptible to plating by said electroless metal plating solution.

9. The method of claim 8 wherein said electric potential is increased from zero at a linear rate of increase.

10. The method of claim 7 wherein the polarity of said one electrode composed of a metal susceptible to plating by said electroless metal plating solution is positive when said electrical potential is being applied across said electrodes.

11. The method of claims 7, 10 or 9 further comprising the step of correlating the magnitude of said peak current with the magnitudes of peak currents obtained for standard solutions of known absolute plating rates to thereby determine the absolute plating rate of said electroless metal plating solution.

12. The method of defined in claim 7 wherein said solution is an electroless nickel plating solution.

13. The method defined in claim 7 wherein said solution is an electroless copper plating solution.

* * * * *